(12) United States Patent
Bachtler et al.

(10) Patent No.: US 7,928,275 B2
(45) Date of Patent: Apr. 19, 2011

(54) METHOD FOR PRODUCING ACETYLENE

(75) Inventors: Michael Bachtler, Albersweiler (DE);
Kai Rainer Ehrhardt, Speyer (DE);
Christopher P Witte, Prairieville, LA
(US); Michael L. Hayes, Gonzales, LA
(US)

(73) Assignee: BASF SE, Ludwigshafen (DE)

( * ) Notice: Subject to any disclaimer, the term of this patent is extended or adjusted under 35 U.S.C. 154(b) by 276 days.

(21) Appl. No.: 12/278,313

(22) PCT Filed: Feb. 13, 2007

(86) PCT No.: PCT/EP2007/051370
§ 371 (c)(1),
(2), (4) Date: Aug. 5, 2008

(87) PCT Pub. No.: WO2007/096271
PCT Pub. Date: Aug. 30, 2007

(65) Prior Publication Data
US 2009/0023970 A1   Jan. 22, 2009

Related U.S. Application Data

(60) Provisional application No. 60/775,158, filed on Feb. 21, 2006.

(51) Int. Cl.
*C07C 2/76* (2006.01)
(52) U.S. Cl. ........ 585/541; 585/534; 585/538; 585/539; 585/540; 585/921; 585/922
(58) Field of Classification Search .......... 585/534, 585/538, 540, 541
See application file for complete search history.

(56) References Cited

U.S. PATENT DOCUMENTS

| | | | | |
|---|---|---|---|---|
| 2,692,902 A | * | 10/1954 | Pichler et al. | 585/539 |
| 2,822,411 A | | 2/1958 | Braconier et al. | |
| 4,072,477 A | * | 2/1978 | Hanson et al. | 95/71 |
| 4,426,041 A | * | 1/1984 | Nieuwkamp et al. | 239/468 |
| 4,767,569 A | | 8/1988 | Brophy et al. | |
| 5,804,689 A | * | 9/1998 | Schodel et al. | 585/539 |
| 5,824,834 A | * | 10/1998 | Bachtler et al. | 585/540 |
| 2005/0268781 A1 | * | 12/2005 | Cheney et al. | 95/161 |

OTHER PUBLICATIONS

Pässler, et al., "Acetylene—Production" in Ullmann's Encyclopedia of Industrial Chemistry, 6th Edition, 2000 Electronic Release, Chapter 4.2.1.*
Bloch, "Rotary Screw Compressors" in A Practical Guide to Compressor Technology, 1996, McGraw-Hill.*
Bohnet, Matthias et al., "Ullmann's Encyclopedia of Industrial Chemistry", Sixth Com. Rev. Ed., vol. 1, pp. 225-231, XP-002442775, (2003).
Paessler, Peter et al., "Ullmann's Encyclopedia of Industrial Chemistry", Electronic Release, Acetylene-Production, Sixth Edition, Chapter 4.2.1, pp. 1-3 and p. 1, (2000).

* cited by examiner

*Primary Examiner* — Glenn A Caldarola
*Assistant Examiner* — Bradley Etherton
(74) *Attorney, Agent, or Firm* — Oblon, Spivak, McClelland, Maier & Neustadt, L.L.P.

(57) ABSTRACT

Process for the preparation of acetylene from hydrocarbons by partial oxidation, arc cleavage or pyrolysis, the material stream comprising the acetylene and soot obtained being fed to a compressor, wherein a liquid which takes up the major part of the soot present in the material stream is sprayed into the compressor.

20 Claims, 1 Drawing Sheet

Drawing 1
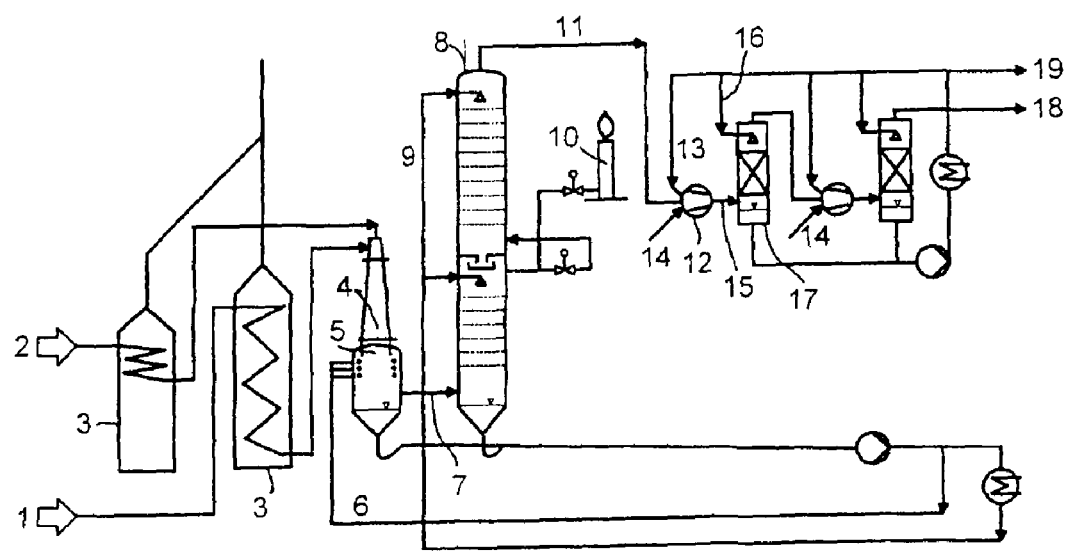

METHOD FOR PRODUCING ACETYLENE

The present invention relates to an improved process for the preparation of acetylene from hydrocarbons by partial oxidation, arc cleavage or pyrolysis, the material stream comprising the acetylene and soot obtained being fed to a compressor.

Acetylene is produced industrially, inter alia, by the process developed by BASF, which is based on partial oxidation of hydrocarbons (preferably natural gas) with oxygen. It is described, for example, in U.S. Pat. No. 5,824,834 and in "Ullmann's Encyclopedia of Industrial Chemistry, Sixth Edition, 2000, Electronic Release, Chapter 4.2.1".

The two feedstocks hydrocarbon and oxygen are first preheated, to about 500 to 650° C. when natural gas is used, and they are then mixed and indeed thereafter reacted in the combustion chamber in a flame which is stabilized by the so-called burner block. Preheating and premixing are required for high acetylene yields.

The flame reaction at temperatures above about 1500° C. is quenched by spraying in water after a few milliseconds, i.e. the very rapid cooling to about 90° C. stops the free radical chain reaction in the flame. This prevents the degradation of the thermo-dynamically unstable intermediate acetylene. The reaction product is so-called cleavage gas, which is a mixture of acetylene, crude synthesis gas (mainly $H_2$ and CO), steam and byproducts. One of the byproducts here is soot. Before the compression, the cleavage gas is usually cooled to about 30-50° C. in order to condense the major part of the steam and thus to reduce the amount of gas to be compressed.

The soot formed as a byproduct proves to be troublesome in the subsequent process stages and efforts are therefore made to separate it from the cleavage gas in order to increase the effectiveness of the process.

The soot forms in the flame during the partial oxidation of the hydrocarbons. Since the soot is formed in the gas phase, it comprises very fine particles which are usually smaller than 1 µm. The amount of soot formed is dependent on the procedure in the reactor, as described in U.S. Pat. No. 5,824,834. The major part of the soot is deposited by the water in the burner quench and in the downstream cooling column. The amount of soot which is then however still present in the cleavage gas to be compressed is still considerable; in the BASF process, it is usually present in a concentration of about 100 to 1000 mg/m$^3$ (S.T.P.) but may also be present in a substantially larger amount in other processes. In order to avoid damage to the compressor used for compressing the gas, according to the prior art the soot is deposited before the compression of the cleavage gas, the soot content in the purified cleavage gas being below about 20 mg/m$^3$ (S.T.P.). For example, wet electrofilters can be used for the deposition.

After the soot removal and the cooling of the cleavage gas, screw compressors are usually used for compressing the cleavage gas, as manufactured, for example, by the companies GE Oil and Gas, Inc., 3300 Medaust Drive, Oshkosh, Wis. 54902, USA, MAN Turbomaschinen AG, 46145 Oberhausen, Germany, or Kobe Steel, LTD., Compressor division, 9-12, Kita-shinagawa 5-chrome, Shinagawa-ku, Tokyo, 141-8688, Japan. These expensive machines manufactured with high precision are preferably used since they are also capable of compressing gases which have a tendency to form polymer deposits. During the operation, a small amount of water for cooling is added to the compressor, but this water evaporates during the compression (i.e. in the machine), usually completely, and the screw compressors are therefore operated "dry".

Owing to its extreme fineness, the deposition of the soot is a very demanding separation task which consequently entails high capital costs and very complex process engineering. Furthermore, the wet electrofilters usually used constantly cause interruptions to operation particularly for the deposition of acetylene black. Frequent causes are, for example, broken spray wires, the organic acids present in the cleavage gas being one of the factors responsible for this, and the formation of deposits, which are promoted by the poor wetting of the soot by water.

It was therefore the object to provide an improved process for the preparation of acetylene which avoids said disadvantages and which permits the preparation of acetylene in an effective manner using simple process engineering and with high availability and long on-stream times.

Accordingly, a process for the preparation of acetylene from hydrocarbons by partial oxidation, arc cleavage or pyrolysis was found, the material stream comprising the acetylene and soot obtained being fed to a compressor, wherein a liquid which takes up the major part of the soot present in the material stream is sprayed into the compressor.

It was surprisingly found that the screw compressors preferably used as the compressor are capable of depositing considerable amounts of soot from the cleavage gas if water is sprayed in at the entrance in an amount such that water in liquid form, in which the deposited soot is dispersed, emerges from the compressor. According to the invention, the solid deposition and not the gas cooling consequently determines the amount of water sprayed in. As a result, an apparatus for depositing the soot (usually the electrofilter) can advantageously be dispensed with, and, according to the invention, the cleavage gas stream can thus be fed directly onto the screw compressor. Further process steps may be connected between reactor and compressor if the presence of soot permits this. Preferably, the cleavage gas stream is cooled in an additional column before the compression and simultaneous soot deposition, in order to reduce the volume stream to be compressed by condensation of steam and in order to reduce the temperature at the compressor exit. The elimination of the soot separator (usually electrofilter) substantially simplifies the effort in the case of a new plant and significantly reduces the capital costs. Furthermore, the availability is increased for all plants because the susceptible electrofilter need no longer be operated, and the effectiveness of the entire process is increased.

The person skilled in the art would not have contemplated such a procedure since screw compressors are very expensive apparatuses manufactured with high precision. Thus, for example, firstly large dimensioning of the screws is required in the for the gas streams prevailing here and secondly, in spite of these considerable dimensions, a constant minimum distance must be ensured between the screws rotating at very high speed, which distance is of the order of magnitude of a few $1/100$ mm. In the operation of these expensive machines with high solids content, as indeed the cleavage gas stream still has after leaving the cooling column, damage to this apparatus was to be feared. Surprisingly, however, the liquid, preferably water, sprayed in in excess ensures that continuous operation is possible.

The deposition, according to the invention, of the soot takes place particularly well and without faults in the long term if the soot content of the water which leaves the screw compressor in liquid form (without steam) is from 0.05 to 5% by weight, preferably from 0.1 to 1.5% by weight and particularly preferably from 0.15 to 0.8% by weight. Higher soot contents should be avoided because, owing to the extremely small size of the soot, the viscosity of the soot/water suspension otherwise increases excessively. Lower soot contents would require the addition of water or less cooling of the steam-saturated cleavage gas. This condition defines firstly the minimum amount of water to be sprayed in at the compressor entrance and secondly the maximum soot content in the water sprayed in. A cause of the deposition is the very intensive mixing and interaction (in the end relative velocity) between the finely divided soot particles present in the cleavage gas on the one hand and the water on the other hand, which is also decisive in the case of other separators, such as Venturi scrubbers.

In a preferred embodiment, a water circulation exists in order to reduce the water consumption. As a result of the circulation, the process water comprises soot. It can also be used, for example, in a cooling column downstream of the compressor. In order to limit the soot content in the water circulation according to the above condition the soot separated off from the cleavage gas must be discharged. This can be effected, for example, in the form of a soot/water suspension (process water), which is discharged from the process.

In order to ensure sufficient deposition, the compression ratio must be at least 1:2 and preferably at least 1:3.

In a further embodiment of the process according to the invention, the screw compressor can also be operated by spraying in oil instead of spraying in water. Here too, the soot deposition according to the invention can be effected. In contrast to water, the oil can take up at most about 20% by weight of soot. When oil is sprayed in, the compressor is usually operated with a large oil excess so that the evaporation presents no problem.

Analogously, further liquids in addition to oil and water are suitable according to the invention, such as, for example, N-methylpyrrolidone, methanol, acetone, gasoline, benzene or dimethylformamide. Preferably used substances are those which are already used in the various acetylene processes, i.e. N-methylpyrrolidone in the BASF process. The maximum soot content in the liquid emerging from the compressor depends on the respective material properties. Finally, the viscosity of the respective suspension must be comparable with the abovementioned water/soot suspensions.

The soot is preferably virtually completely deposited during the compression of the cleavage gas. In the process according to the invention, residual soot contents of less than about 20 mg/Nm$^3$ (S.T.P.) can be achieved in the gas stream leaving the compressor; depending on the design of the process according to the invention, even substantially lower residual soot contents can be achieved. Compared with the use of electrofilters, no difference is detectable with respect to the degrees of deposition of the soot. If appropriate, traces of soot which remain in the cleavage gas are taken up by the solvent (N-methylpyrrolidone) which is used for the subsequent separation of the cleavage gas. Since, owing to polymer formation, the solvent has to be regenerated continuously or at least regularly, the traces of soot do not present any problems.

For trouble-free operation in the long term, it is advisable, particularly in a preferred embodiment of the process, always to keep the intake muffler upstream of the compressor and the intake screen moist in order to prevent soot deposits. For the conventional removal of soot deposits, the acetylene production must be interrupted in the case of single-train plants and must be reduced in the case of multitrain plants.

The process according to the invention can be used both for a closed water quench according to U.S. Pat. No. 5,824,834 and open water quench as described in Ullman. The process can also be applied to the other known processes for the preparation of acetylene, as described, for example, in Ullman.

The process according to the invention permits economical preparation of acetylene. The separation of the soot obtained here as a byproduct is effected in a manner which is simple in terms of process engineering and involves little effort, it being possible simultaneously to achieve long on-stream times in the production. With the preferred use of water as added liquid another advantage proves to be that no further components foreign to the system are fed to the process.

EXAMPLE

A description of the BASF process comprising a water quench is to be found in Ullman. According to U.S. Pat. No. 5,824,834, the mode of operation of the plant was modified so that recycling of the process water in a closed system was permitted and contact of the pollutant-laden process water with the atmosphere could thus be prevented.

FIG. 1 shows an embodiment of the process according to the invention. The feedstocks natural gas (1) and oxygen (2) are preheated in fired preheaters (3). They are mixed in the mixing zone (4) and reacted in a flame reaction in the combustion chamber (5). The flame is quenched below the combustion chamber by spraying in process water (6). The so-called cleavage gas (7), here the material stream which comprises the acetylene and the soot, enters the cooling column (8) approximately at the limiting cooling temperature and saturated with steam. In said cooling column, the cleavage gas is cooled with the aid of cooled process water (9), and a major part of the steam is thus condensed. The flare (10) is required for startup and rundown processes. The cleavage gas (11) cooled to about 40° C. (45 000 m$^3$ (S.T.P)/h dry), which comprises 200 mg/m$^3$ (S.T.P.) of soot, is subsequently compressed with the aid of a two-stage screw compressor (12), first from 1.1 to 4.2 and then to 11 bar (abs), the soot being deposited. 7.5 m$^3$/h of process water (13) which comprises 0.15% by weight of soot are sprayed into each stage of the compressor. For sealing from the atmosphere, demineralized water (14) is used as so-called sealing liquid, in addition to nitrogen, with the result that 4 m$^3$/h enter the process water circulation. At the exit of the first stage (15), the temperature is 85° C. and the soot content of the water is 0.22% by weight. After each compression stage the cleavage gas is cooled to 40° C. by means of cooled process water (16) in cooling columns (17). After the compression, the cleavage gas (18) is separated into its constituents, for example as described in Ullman. The water which was condensed during the compression and subsequent cooling and the demineralized water introduced into the circulation are discharged (19) together with the soot present. The soot content in the water circulation depends on the amount of water introduced into the circulation (condensed steam+demineralized water) and amount of soot deposited, which correspond to the amounts discharged as soot/water suspension.

In a further working example, the startup screens before the entrance to the two compressor stages and after the intake mufflers remain permanently installed. The screens prevent damage to the compressor by the penetration of foreign bodies, such as screws, which originate from assembly or maintenance activities. The startup screen at the entrance of the first compressor stage is sprayed with 2 m$^3$/h of water in order to prevent the formation of soot deposits. A commercial airless high-pressure solid-cone nozzle is suitable for this purpose and was operated at an admission pressure of 5 bar. The opening angle and the distance from the startup screen was chosen so that as uniform and complete a wetting as possible is ensured. If appropriate, a high flow velocity of the cleavage gas is taken into account here. Without spraying in water, the startup screen had to be cleaned for three months, with the result that the acetylene production has to be interrupted in the case of single-train plants and has to be reduced in the case of multitrain plants. The startup screen of the second stage does not have to be kept moist in the working example. Consequently, the soot is already virtually completely deposited in the first stage.

We claim:

1. In a process for the preparation of acetylene from hydrocarbons by partial oxidation, arc cleavage or pyrolysis, wherein cleavage gas comprising acetylene and soot byproduct obtained by partial oxidation, arc cleavage or pyrolysis is fed to a compressor, the improvement wherein liquid water which takes up the major part of the soot present in the cleavage gas is sprayed into the compressor at the entrance in an amount such that water in liquid form, in which the soot is dispersed, emerges from the compressor with a soot content of from 0.05 to 5% by weight.

2. The process according to claim 1, wherein one or more one-stage or multistage screw compressors are used as the compressor.

3. The process according to claim 1, wherein the compression ratio is at least 1:2.

4. The process according to claim 1, wherein the compression ratio is at least 1:3.

5. The process according to claim 1, wherein the water emerging from the compressor has a soot content of from 0.1 to 1.5% by weight.

6. The process according to claim 1, wherein the water emerging from the compressor has a soot content of from 0.15 to 0.8% by weight.

7. The process according to claim 1, wherein the soot-free liquid water seals the compressor from the environment.

8. The process according to claim 1, wherein soot deposits on the intake screen upstream of the compressor and/or on the intake muffler upstream of the compressor are prevented by continuous or discontinuous moistening the intake screen and/or intake muffler with the liquid water.

9. The process according to claim 8, wherein the liquid water is sprayed continuously onto the intake screen or intake muffler using a solid-cone nozzle.

10. The process according to claim 1, further improved by eliminating the use of a soot separator from the process prior to feeding the cleavage gas to the compressor.

11. The process according to claim 1, wherein the cleavage gas is cooled to about 30-50° C. prior to being sprayed into the compressor.

12. The process according to claim 1, wherein the cleavage gas obtained by partial oxidation, arc cleavage or pyrolysis is cooled and fed directly into the compressor.

13. In a process for the preparation of acetylene from hydrocarbons by partial oxidation, arc cleavage or pyrolysis, wherein cleavage gas comprising acetylene and soot byproduct obtained by partial oxidation, arc cleavage or pyrolysis is fed to a compressor, the improvement wherein liquid oil which takes up the major part of the soot present in the cleavage gas is sprayed into the compressor at the entrance in an amount such that oil in liquid form, in which the soot is dispersed, emerges from the compressor.

14. The process according to claim 13, wherein the soot-free liquid oil seals the compressor from the environment.

15. The process according to claim 13, further improved by eliminating the use of a soot separator from the process prior to feeding the cleavage gas to the compressor.

16. The process according to claim 13, wherein the cleavage gas obtained by partial oxidation, arc cleavage or pyrolysis is cooled and fed directly into the compressor.

17. In a process for the preparation of acetylene from hydrocarbons by partial oxidation, arc cleavage or pyrolysis, wherein cleavage gas comprising acetylene and soot byproduct obtained by partial oxidation, arc cleavage or pyrolysis is fed to a compressor, the improvement wherein a liquid solvent selected from the group consisting of N-methylpyrrolidone, methanol, acetone, gasoline, benzene, and dimethylformamide which takes up the major part of the soot present in the cleavage gas is sprayed into the compressor at the entrance in an amount such that the solvent in liquid form, in which the soot is dispersed, emerges from the compressor.

18. The process according to claim 17, wherein, after the compression of the cleavage gas, the solvent is used for the separation thereof.

19. The process according to claim 17, wherein the cleavage gas obtained by partial oxidation, arc cleavage or pyrolysis is cooled and fed directly into the compressor.

20. The process according to claim 17, further improved by eliminating the use of a soot separator from the process prior to feeding the cleavage gas to the compressor.

* * * * *